(12) United States Patent
Pasbrig et al.

(10) Patent No.: US 7,854,225 B2
(45) Date of Patent: Dec. 21, 2010

(54) BLISTER PACKAGE FOR INHALABLE MEDICAMENT

(75) Inventors: Erwin Pasbrig, Singen (DE); Richard Ian Walker, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 784 days.

(21) Appl. No.: 10/533,332

(22) PCT Filed: Oct. 30, 2003

(86) PCT No.: PCT/EP03/12159
§ 371 (c)(1),
(2), (4) Date: May 2, 2005

(87) PCT Pub. No.: WO2004/041672
PCT Pub. Date: May 21, 2004

(65) Prior Publication Data
US 2006/0102511 A1 May 18, 2006

(30) Foreign Application Priority Data
Nov. 2, 2002 (GB) ................ 0225621.2

(51) Int. Cl.
B65D 75/36 (2006.01)
(52) U.S. Cl. .................. 128/203.15; 206/531
(58) Field of Classification Search ........... 128/203.15, 128/203.21, 203.12; 604/58; 428/35.2–36.7; 53/432, 440; 206/531
See application file for complete search history.

(56) References Cited

U.S. PATENT DOCUMENTS

| | | | |
|---|---|---|---|
| 3,809,221 A | 5/1974 | Compere | |
| 3,836,425 A * | 9/1974 | Whiting, Jr. | ............ 428/213 |
| 3,924,747 A | 12/1975 | Gerner | |
| 4,211,326 A | 7/1980 | Hein et al. | |
| 4,588,090 A | 5/1986 | Spuck et al. | |
| 4,781,294 A | 11/1988 | Croce | |
| 4,797,253 A | 1/1989 | Peterson | |
| 5,091,261 A | 2/1992 | Casey et al. | |
| 5,139,878 A | 8/1992 | Long et al. | |

(Continued)

FOREIGN PATENT DOCUMENTS

CH 0689589 A5 6/1999

(Continued)

OTHER PUBLICATIONS

European Patent Application No. 03772284.0-2308 Prosecution History (EP1556292).

*Primary Examiner*—Steven O Douglas
(74) *Attorney, Agent, or Firm*—Dwight S. Walker (57) ABSTRACT

There is provided a blister form medicament pack comprising (a) a base sheet in which blisters are formed to define pockets therein for the containment of inhalable medicament; and (b) a lid sheet which is sealable to the base sheet except in the region of the blisters and mechanically peelable from the base sheet to enable release of said inhalable medicament. The base sheet and/or said lid sheet have a laminate structure comprising (a) a first layer of aluminum foil; and (b) a second layer of polymeric material of thickness from 10 to 60 micron, said polymeric material having a water vapor permeability of less than 0.6 g/(100 inches$^2$) (24 hours) (mil) at 25° C.

33 Claims, 2 Drawing Sheets

U.S. PATENT DOCUMENTS

| | | |
|---|---|---|
| 5,236,749 A | 8/1993 | Ewing |
| 5,343,672 A | 9/1994 | Kearney et al. |
| 5,469,968 A | 11/1995 | Matthews et al. |
| 5,484,631 A | 1/1996 | Hoh |
| 5,486,390 A | 1/1996 | Burns et al. |
| 5,522,506 A | 6/1996 | Roulin et al. |
| 5,589,275 A | 12/1996 | Breitler et al. |
| 5,729,958 A | 3/1998 | Kerney et al. |
| 5,783,273 A | 7/1998 | Yamamoto et al. |
| 5,803,248 A | 9/1998 | Cox |
| 5,830,547 A | 11/1998 | MacKenzi et al. |
| 5,871,831 A | 2/1999 | Zeiter et al. |
| 5,911,325 A | 6/1999 | Breitler |
| 5,932,338 A | 8/1999 | Schnabele et al. |
| 6,270,869 B1 | 8/2001 | Breitler et al. |
| 6,337,113 B1 | 1/2002 | Pasbrig et al. |
| 6,880,722 B2 * | 4/2005 | Anderson et al. ............ 221/71 |

FOREIGN PATENT DOCUMENTS

| | | |
|---|---|---|
| DE | 2907107 A1 | 3/1980 |
| DE | 4236450 A1 | 10/1992 |
| DE | 4243094 C2 | 4/1995 |
| DE | 4414669 C2 | 4/1996 |
| DE | 19613960 C2 | 10/1998 |
| DE | 19828857 A1 | 12/1999 |
| DE | 19828858 A1 | 12/1999 |
| DE | 19828867 A1 | 12/1999 |
| EP | 0118975 A1 | 9/1984 |
| EP | 0466068 A2 | 7/1991 |
| EP | 0646367 | 4/1995 |
| EP | 0765741 A2 | 4/1997 |
| EP | 0845350 | 6/1998 |
| EP | 0845350 A | 6/1998 |
| EP | 905042 A1 | 3/1999 |
| EP | 0920989 A2 | 6/1999 |
| EP | 968817 A2 | 4/2000 |
| EP | 1038792 | 9/2000 |
| EP | 838293 B1 | 7/2004 |
| EP | 1556292 B1 | 7/2005 |
| FR | 2660634 A1 | 10/1991 |
| FR | 2770207 | 4/1999 |
| GB | 2277920 | 11/1994 |
| JP | 59182733 | 10/1984 |
| JP | 61144341 | 7/1986 |
| JP | 61258750 | 11/1986 |
| JP | 04135752 | 5/1992 |
| JP | 04166544 | 6/1992 |
| JP | 05178365 | 7/1993 |
| JP | 06226935 | 8/1994 |
| JP | 07041044 | 2/1995 |
| JP | 07256842 | 10/1995 |
| JP | 08001766 | 1/1996 |
| JP | 08113264 | 5/1996 |
| JP | 08192870 | 7/1996 |
| JP | 09011422 | 1/1997 |
| JP | 10024960 | 1/1998 |
| JP | 10077067 | 3/1998 |
| JP | 10095456 | 4/1998 |
| JP | 10315408 | 12/1998 |
| JP | 11138725 | 5/1999 |
| JP | 11193065 | 7/1999 |
| JP | 11198295 | 7/1999 |
| JP | 2000-0015750 | 1/2000 |
| JP | 2000-0017088 | 1/2000 |
| JP | 200007022 | 1/2000 |
| WO | 9425364 | 4/1994 |
| WO | 9425364 | 11/1994 |
| WO | 9607601 | 3/1996 |
| WO | 9625254 | 8/1996 |
| WO | 9714629 | 4/1997 |
| WO | 9719811 | 6/1997 |
| WO | 9724395 | 7/1997 |
| WO | 9800352 | 1/1998 |
| WO | 9832674 | 7/1998 |
| WO | 9836902 A1 | 8/1998 |
| WO | 9852737 | 11/1998 |
| WO | 0009596 | 2/2000 |
| WO | 0189445 | 11/2001 |
| WO | 0198174 | 12/2001 |

* cited by examiner

BLISTER PACKAGE FOR INHALABLE MEDICAMENT

CROSS-REFERENCE TO RELATED APPLICATIONS

This application is filed pursuant to 35 U.S.C. § 371 as a United States National Phase Application of International Application No. PCT/EP2003/012159 filed Oct. 30, 2003, which claims priority from GB 0225621.2 filed Nov. 2, 2002.

TECHNICAL FIELD

The present invention relates to a medicament carrier in peelable blister pack form suitable for containing medicament for inhaled delivery to the lung.

BACKGROUND OF THE INVENTION

The use of medicament dispensers in the delivery of medicaments to the lung is well known. Such dispensers generally comprise a body or housing within which a medicament carrier is located. Known inhalation devices include those in which the medicament carrier is in blister pack form (e.g. an elongate blister strip) containing a number of discrete doses of powdered medicament. In use, the blister pack is typically housed within the dispenser in such a way that the blisters may be transported through the dispenser in indexed fashion to enable accessing of the discrete doses of medicament carried thereby. Such devices usually contain a mechanism of individually accessing the doses contained within the blisters. Known access mechanisms typically comprise either blister piercing means or means to peel a lid sheet away from a base sheet of the blister pack. The powdered medicament can then be accessed and inhaled.

It is desirable that elongate blister strip form medicament carriers for containing medicament in dry powder form have suitable moisture transfer properties. Whilst to an extent, the optimal character of such properties is dependent on the nature of the particular medicament formulation to be carried within the blister it is generally beneficial for the material of the strip and of any seals made thereto to either prevent or at least to significantly slow down moisture ingress to the medicament contained within the blister to prevent the moisture-induced degradation or agglomeration thereof. Reducing moisture permeation reduction to the cavity of the blister pack and thereby enhancing the stability of the medicament contained therein are particular targets of interest. Efforts therefore continue to be expended in the development of improved strip materials, pack forms and sealing methods.

Conventional high barrier medicament blister packs typically comprise aluminium foil sheets in both the lid sheet and base sheet components thereof. The aluminium sheets are selected to have sufficient thickness to be substantially free of 'pinhole' imperfections thereby making them essentially impermeable to the transfer of moisture. In developments thereof, laminate form sheets are used for either one or both of the lid and base sheets, which laminates typically comprise a layer of aluminium foil and one or more polymeric layers. Such laminates are typically employed when a 'cold form' method is employed to form the base sheet with blister pockets. Polyvinyl chloride (PVC) is conventionally used as the material of the polymeric layer.

The Applicants have now appreciated that such polymeric layers act as the principal conduit for moisture ingress to the medicament contained within the blisters. The absolute rate of flow of moisture is dependent on various factors including prevailing environmental conditions, the polymer material and properties of the medicament itself (e.g. hygroscopic or desiccant properties).

The Applicants have now found that moisture ingress to the interior of the blister may be reduced by the selection of particular, unconventional polymeric materials for use in the laminate sheets of the blister packs. The Applicants have also found that moisture ingress may also be reduced by the use of polymeric layers in the laminates, which have reduced thickness compared to conventional polymeric layers. Enhancements in the storage stability of dry powder form medicament contained within the blister packs may thereby be achieved.

The Applicants have further found that certain of the new polymeric materials can act to provide an enhanced oxygen barrier. That is to say, the layer comprising the new polymeric material acts such as to reduce oxygen permeation, and thereby also reduce oxygen ingress to the medicament contained within the blister. This can be important where the medicament is susceptible to oxidative degradation, The Applicants have also further found that certain of the new polymeric materials can act to modify the static electricity-related properties of the laminates and blister pack. This can be important where the powder form medicament is susceptible to adhere to the interior of a blister cavity because of static electricity effects thereby affecting the ability to release/deliver the powder from an opened blister pack.

SUMMARY OF THE INVENTION

According to one aspect of the invention there is provided a blister form medicament pack comprising
(a) a base sheet in which blisters are formed to define pockets therein for the containment of inhalable medicament;
(b) a lid sheet which is sealable to the base sheet except in the region of the blisters and mechanically peelable from the base sheet to enable release of said inhalable medicament, wherein said base sheet and/or said lid sheet have a laminate structure comprising (a) a first layer of aluminium foil; and (b) a second layer of polymeric material of thickness from 10 to 60 micron, said polymeric material having a water vapour permeability of less than 0.6 g/(100 inches$^2$) (24 hours) (mil) at 25° C.

The water vapour permeability is suitably measured by ASTM test method no. ASTM E96-635 (E).

Suitably, the polymeric material comprises a material selected from the group consisting of polypropylene (e.g. in oriented or cast form; standard or metallocene); polyethylene (e.g. in high, low or intermediate density form); polyvinylidene chloride (PVDC); polychlorotrifluoroethylene (PCTFE); cyclic olefin copolymer (COC); and cyclic olefin polymer (COP).

Where the polymeric material is selected from the group consisting of polyethylene (in high density form), polypropylene or polyvinylidene chloride (PVDC), reduced oxygen permeation through the polymeric layer, and hence to the interior of the blister, may be achieved. Oxygen permeation through the polymeric layer may be tested using ASTM test method D3985-81, in which such oxygen transmission is measured at 25° C. and 50% Relative Humidity.

The medicament carrier has a blister pack form, particularly a blister strip having multiple distinct blister portions provided along its length. The blisters may have any suitable shape including those with a square, circular or rectangular profile.

The medicament carrier suitably has multiple distinct (i.e. separate) medicament doses carried thereby, and may for example, be in the form of a peelable blister strip, disk or other suitable blister pack form.

The medicament carrier is in the form of a peelable blister pack, particularly an elongate form peelable blister strip. The peelable blister pack comprises a base sheet in which blisters are formed to define pockets therein for the containment of inhalable medicament and a lid sheet which is hermetically sealed to the base sheet except in the region of the blisters in such a manner that the lid sheet and the base sheet can be peeled apart to enable release of the inhalable medicament from one or more pockets thereof. The term 'inhalable medicament' is used herein to mean medicament suitable for inhaled delivery to the lung.

The base and lid sheets are typically sealed to one another over their whole width except for the forward end portions where they are typically not sealed to each other at all. Thus, separate base and lid sheet forward end portions are presented at the end of the strip.

The lid sheet and/or base sheet of the medicament carrier herein are in the form of a laminate, which comprises multiple layers of different materials.

The base sheet and/or lid sheet herein comprises (a) a first layer of metal foil, particularly aluminium foil; and (b) a second layer of polymeric material having a water vapour permeability of less than 0.6 g/(100 inches$^2$) (24 hours) (mil) at 25° C.

The second layer comprises a polymeric material of low water vapour permeability. The water vapour permeability is less than 0.6 g/(100 inches$^2$) (24 hours) (mil) at 25° C., but preferably less than less than 0.3 g/(100 inches$^2$) (24 hours) (mil) at 25° C. as suitably measured by ASTM E96-635 (E) which defines a standard test method for measuring water vapour permeability.

The second layer of the base sheet and/or lid sheet is generally an inner layer of the overall medicament carrier pack.

Suitably, the polymeric material is selected from the group consisting of polypropylene (in oriented or cast form; standard or metallocene); polyethylene (in high, low or intermediate density form); polyvinylidene chloride (PVDC); polychlorotrifluoroethylene (PCTFE); cyclic olefin copolymer (COC); and cyclic olefin polymer (COP). Optionally, other layers of material are also present.

Material sold under the trade name Aclar by Honeywell Inc, a United States corporation is a suitable polychlorotrifluoroethylene (PCTFE) polymeric material herein. Suitable cyclic olefin copolymer (COC) is sold by Hoechst AG of Germany, under the trade name Topaz. A suitable cyclic olefin polymer is sold by Nippon Zeon Co. Ltd of Tokyo, Japan under the trade name Zenor.

Suitably polypropylene polymeric material is manufactured by a process in which a one or more metallocene compounds is employed to modify and/or control the nature of any side-chain groups thereof.

The thickness of the second layer of polymeric material is from 10 to 60 micron. Preferably, the thickness of the polymeric layer is optimised to reduce moisture ingress, and particularly is from 20 to 30 micron.

Suitably, the lid sheet comprises at least the following successive layers: (a) paper; bonded to (b) plastic film; bonded to (c) aluminium foil.

The aluminium foil typically coated with a layer (e.g. of heat seal lacquer; film or extrusion coating) for bonding to the base sheet material.

The thickness of each of the layers of the lid sheet may be selected according to the desired properties but is typically of the order of from 5 to 200 micron, particularly from 10 to 50 micron.

The plastic layer is in one aspect, suitably selected from polyester (non-oriented, monaxial, or biaxial oriented), polyamide, polypropylene or PVC. In another aspect the plastic film is an oriented plastic film, suitably selected from oriented polyamide (OPA); oriented polyester (OPET); and oriented polypropylene (OPP). The thickness of the plastic layer is typically from 5 to 40 μm, particularly 12 to 30 μm.

The thickness of the aluminium layer is typically from 15 to 60 μm, particularly 20 to 40 μm.

In aspects, the paper layer comprises a paper/extrusion layer, optimally laminated to aluminium.

In one particular aspect, the lid sheet comprises at least the following successive layers: (a) paper; bonded to (b) polyester; bonded to (c) aluminium foil; that is coated with a heat seal lacquer for bonding to the base sheet. The thickness of each layer may be selected according to the desired properties but is typically of the order of from 5 to 200 micron, particularly from 10 to 50 micron.

The bonding may in aspects be provided as an adhesive bond (e.g. solvent-based adhesive wherein the solvent is organic or water-based); solvent free adhesive bond; extrusion laminated bond; or heat calendaring.

In another particular aspect, the base sheet comprises at least the following successive layers: (a) oriented polyamide (OPA); adhesively bonded to (b) aluminium foil; adhesively bonded to (c) a third layer of thickness from 10 to 60 micron comprising a polymeric material. The polymeric material has a water vapour permeability of less than 0.6 g/(100 inches$^2$) (24 hours) (mil) at 25° C. The third layer will bond with the lid sheet, which is generally treated with a heat seal lacquer.

The thickness of each non-polymeric layer of the base sheet may be selected according to the desired properties but is typically of the order of from 5 to 200 micron, particularly from 40 to 60 micron. In accord with the invention, the thickness of the polymeric layer is selected to reduce moisture ingress, and is from 10 to 60 micron, more particularly from 20 to 30 micron.

Suitably, the polymeric material is selected from the group consisting of polypropylene (in oriented or cast form; standard or metallocene); polyethylene (in high, low or intermediate density form); polyvinylidene chloride (PVDC); polychlorotrifluoroethylene (PCTFE); cyclic olefin copolymer (COC); and cyclic olefin polymer (COP). Optionally, other layers of material are also present.

One particular base sheet comprises the following successive layers: (a) oriented polyamide (OPA); adhesively bonded to (b) aluminium foil; adhesively bonded to (c) oriented polypropylene (OPP). The thickness of the polymeric layer is from 10 to 60 micron, particularly from 20 to 30 micron.

Another particular base sheet comprises the following successive layers: (a) oriented polyamide (OPA); adhesively bonded to (b) aluminium foil; adhesively bonded to (c) cast polypropylene. The thickness of the polymeric layer is from 10 to 60 micron, particularly from 20 to 30 micron.

A further particular base sheet comprises the following successive layers: (a) oriented polyamide (OPA); adhesively bonded to (b) aluminium foil; adhesively bonded to (c) high density polyethylene (HDPE). The thickness of the polymeric layer is from 10 to 60 micron, particularly from 35 to 45 micron.

A further particular base sheet comprises the following successive layers: (a) oriented polyamide (OPA); adhesively bonded to (b) aluminium foil; adhesively bonded to (c) low density polyethylene (LDPE). The thickness of the polymeric layer is from 10 to 60 micron, particularly from 20 to 30 micron.

A further particular base sheet comprises the following successive layers: (a) oriented polyamide (OPA); adhesively bonded to (b) aluminium foil; adhesively bonded to (c) polyvinylidene chloride (PVDC). The thickness of the polymeric layer is from 10 to 60 micron, particularly from 20 to 30 micron. The grade of the PVDC is generally from 8 to 95 gsm, particularly from 10 to 40 gsm.

A further particular base sheet comprises the following successive layers: (a) oriented polyamide (OPA); adhesively bonded to (b) aluminium foil; adhesively bonded to (c) polychlorotrifluoroethylene (PCTFE). The thickness of the polymeric layer is from 10 to 60 micron, particularly from 20 to 45 micron.

A further particular base sheet comprises the following successive layers: (a) oriented polyamide (OPA); adhesively bonded to (b) aluminium foil; adhesively bonded to (c) cyclic olefin copolymer (COC). The thickness of the polymeric layer is from 10 to 60 micron, particularly from 20 to 30 micron.

A further particular base sheet comprises the following successive layers: (a) oriented polyamide (OPA); adhesively bonded to (b) aluminium foil; adhesively bonded to (c) cyclic olefin polymer (COP). The thickness of the polymeric layer is from 10 to 60 micron, particularly from 20 to 30 micron.

Various known techniques can be employed to join the lid and base sheet and hence to seal the blisters. Such methods include adhesive bonding, radio frequency welding, ultrasonic welding and hot bar sealing.

The base sheet herein is particularly suitable for forming by 'cold form' methods, which are conducted at lower temperatures than conventional methods (e.g. at close to room temperature). Such 'cold form' methods are of particular utility where the medicament or medicament formulation for containment within the blister is heat sensitive (e.g. degrades or denatures on heating).

One method for forming a medicament carrier herein comprises the steps of (a) providing a base sheet having a first mating surface and a lid sheet a having a second mating surface, the base sheet including at least one blister having a periphery region, the blister being adapted to receive a medicament composition; (b) filling the blister with the pharmaceutical composition; (c) bonding the base sheet to the lid sheet to create a primary seal therebetween. The medicament carrier can be of any shape for good airflow (e.g. to assist aerosolisation of the powder contained therein), preferably, substantially elongated or substantially circular.

Suitably, the base sheet includes at least a first bonding material disposed on the first mating surface and the lid sheet includes at least a second bonding material disposed on the second mating surface. In one embodiment, one or both of the first or second bonding materials comprises at least one polymeric material. In an additional embodiment, one or both of the first or second bonding material comprises a substance that enables peelable separation e.g. a heat seal lacquer, plastic film or coating.

A suitable manufacturing system herein comprises (a) a base transporter for transporting a base sheet to a filling station, the base sheet including at least one blister pocket adapted to receive an inhalable medicament composition, the base sheet further including a first bonding material; (b) a filling apparatus for filling the blister with the inhalable medicament composition; (c) a lid transporter for transporting a lid sheet proximate to the filled base sheet, the lid sheet including a second bonding material; (d) a bonding mechanism for bonding the first and second bonding materials to create a primary seal therebetween.

In use, the medicament carrier is suitably receivable by a medicament dispenser that comprises a housing for receipt of the medicament carrier. In one aspect, the medicament dispenser has unitary form and the housing is integral therewith. In another aspect, the medicament dispenser is configured to receive a refill cassette and the housing forms part of that refill cassette.

Suitably, the interior of the housing is shaped, or alternatively provided with specific guiding features, to guide the medicament carrier appropriately into the housing. In particular, the guiding should ensure that the medicament carrier is suitably located to interact with internal mechanisms (e.g. indexing and opening mechanisms) of the housing.

Suitably, the dispenser has an internal mechanism for dispensing the distinct inhalable medicament doses carried by the medicament carrier for administration to the patient (e.g. by inhalation). Suitably, the mechanism comprises, a) receiving means for receiving the medicament carrier;

b) release means for releasing a distinct medicament dose from the medicament carrier on receipt thereof by said receiving means;

c) an outlet, positioned to be in communication with the medicament dose releasable by said release means;

d) indexing means for individually indexing the distinct medicament doses of the medicament carrier; and The mechanism comprises receiving means (e.g. a receiving station) for receiving the medicament carrier.

The mechanism further comprises release means for releasing a distinct medicament dose from the medicament carrier on its receipt by the receiving station. The release means typically comprises means for mechanically peeling apart the blister strip.

An outlet is positioned to be in communication with the distinct medicament doses releasable by said release means. The outlet may have any suitable form. In one aspect, it has the form of a mouthpiece and in another, it has the form of a nozzle for insertion into the nasal cavity of a patient.

The outlet is preferably a single outlet, which communicates with the distinct medicament dose releasable by said release means via a common air channelling means (e.g. formed as an air-pipe or common manifold). The patient may therefore breathe in through a single outlet, and that breath be transferred through the common channelling means to the released medicament dose, thereby enabling its inhalation.

The mechanism also comprises indexing means for individually indexing the distinct medicament doses of the medicament carrier. Said indexing typically happens in sequential fashion, for example accessing dose portions sequentially arranged along the length of the elongate carrier.

Optionally, the medicament dispenser also includes counting means for counting each time a distinct medicament dose of the medicament carrier is indexed by said indexing means.

In one aspect, counting means is arranged to count each time a distinct medicament dose of the medicament carrier is indexed by said indexing means. Suitably, the indexing means and counting means engage directly or indirectly (e.g. via a coupling) with each other to enable counting of each indexation.

Suitably, the counting means is provided with (or communicates with) a display for displaying to the patient the number of distinct doses left to be taken or the number of doses taken.

In one preferred aspect, the medicament dispenser takes the form of a dispenser for use with a medicament carrier having multiple distinct pockets for containing inhalable medicament doses, wherein said pockets are spaced along the length of and defined between two peelable sheets secured to each other, said dispenser having an internal mechanism for dispensing the medicament doses contained within said medicament carrier, said mechanism comprising,
a) an opening station for receiving a pocket of the medicament carrier;
b) peeling means positioned to engage a base sheet and a lid sheet of a pocket which has been received in said opening station for peeling apart such a base sheet and lid sheet, to open such a pocket, said peeling means including lid driving means for pulling apart a lid sheet and a base sheet of a pocket that has been received at said opening station;
c) an outlet, positioned to be in communication with an opened pocket through which a user can access a medicament dose from such an opened pocket;
d) indexing means for individually indexing the distinct pockets of the medicament carrier.

Suitably, the indexing means comprises a rotatable index wheel having recesses therein, said index wheel being engageable with a medicament carrier in use with said medicament dispenser such that said recesses each receive a respective pocket of the base sheet of a blister strip in use with said medicament dispenser.

According to another aspect of the present invention there is provided a medicament dispenser comprising (e.g. loaded with) at least one medicament carrier wherein.

BRIEF DESCRIPTION OF THE DRAWINGS

The invention will now be described with reference to the accompanying drawings in which.

DETAILED DESCRIPTION OF THE DRAWINGS

Figure 1:
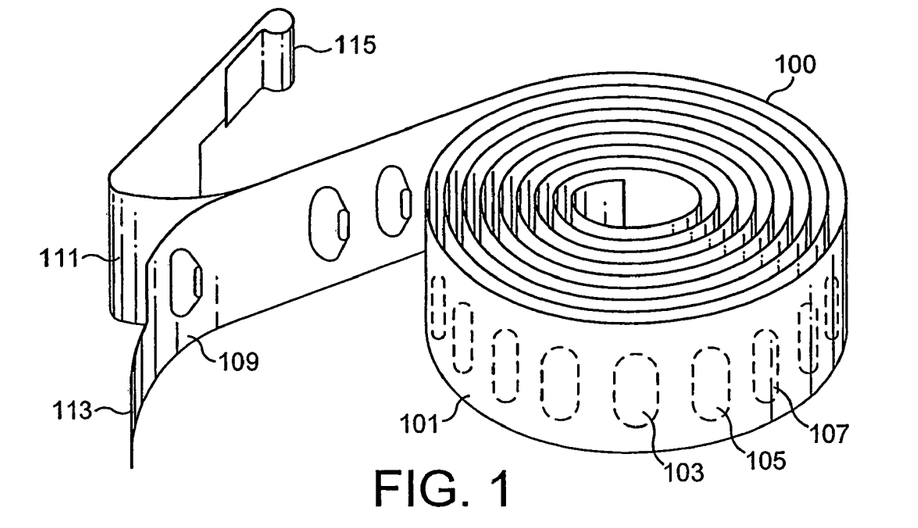
FIG. 1 shows a perspective view of the form of a medicament carrier of a form suitable for use in accord with the present invention.

FIG. 1 shows a medicament carrier 100 that may be constructed to have a detailed form in accord with the present invention. The medicament carrier comprises a flexible strip 101 defining a plurality of pockets 103, 105, 107 each of which would contain a portion of a dose of medicament which can be inhaled, in the form of powder.

The strip comprises a base sheet 109 in which blisters are formed to define the pockets 103, 105, 107 and a lid sheet 111 which is hermetically sealed to the base sheet except in the region of the blisters in such a manner that the lid sheet 111 and the base sheet 109 can be peeled apart. The sheets 109, 111 are sealed to one another over their whole width except for the leading end portions 113, 115 where they are preferably not sealed to one another at all. The lid 111 and base 109 sheets are formed of a laminate and are preferably adhered to one another by heat sealing.

The strip 101 is shown as having elongate pockets 103, 105, and 107 that run transversely with respect to the length of the strip 101. This is convenient in that it enables a large number of pockets 103, 105, 107 to be provided in a given strip 101 length. The strip 101 may, for example, be provided with sixty or one hundred pockets but it will be understood that the strip 101 may have any suitable number of pockets.

Figure 2:
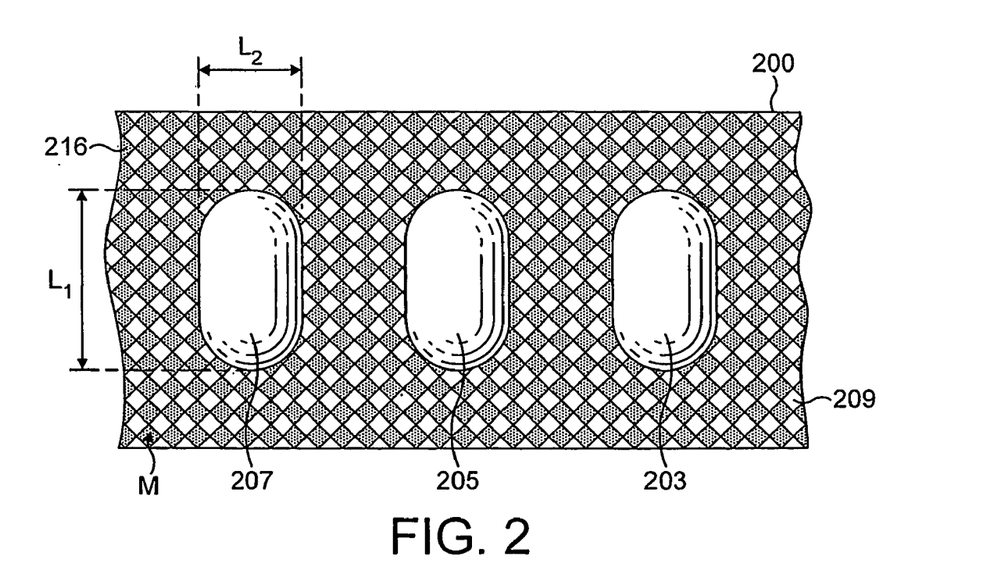
FIG. 2 shows a top view of the form of a medicament carrier of a form suitable for use in accord with the present invention.

Referring now to FIG. 2, there is shown a medicament carrier in the form of a laminate assembly or blister strip 200 viewed from underneath. The blister strip has a substantially elongated shape and includes a plurality of blisters 203, 205, 207 formed in the base 209 thereof adapted to receive a pharmaceutical composition 14, preferably in the form of a dry powder. Each blister 203, 205, 207 has a length $l_1$ that is preferably from 1.5 to 15.0 mm, more preferably, from 1.5 to 8.0 mm, and in an actual embodiment is equal to 7.5 mm, measured along its longer axis, and a width $l_2$ that is preferably from 1.5 to 10.0 mm, more preferably, from 1.5 to 8.0 mm, and in an actual embodiment is equal to 4.0 mm, measured along its shorter axis.

In the illustrated example of FIG. 2, the blister strip 200 has a width of 12.5 mm. The thickness of the base 209 is in the range of 75 to 200 micron. The thickness of the lid is in the range 40 to 100 micron. The combined thickness of the base 209 and lid (not visible) is approximately 115 to 300 micron. The blisters 203, 205, 207 are typically at 7.5 mm spacings along the blister strip 200. Each blister 203, 205, 207 contains an effective dosage of powder, preferably less than 30 mg of powder, more preferably, between 5-25 mg of powder, and most preferably, approximately 12.5 mg of powder. The powder is an inhalable medicament composition comprising at least one medicament active.

Suitable materials are employed to construct the base 209 and lid (not visible). In accord with the invention, the base 209 and/or lid comprise laminate structures having at least one bonding material on at least one mating surface of either the base 209 or lid. The bonding material(s) preferably comprise at least one polymeric material and a heat seat lacquer (e.g. a vinylic heat seal lacquer).

Figure 4:
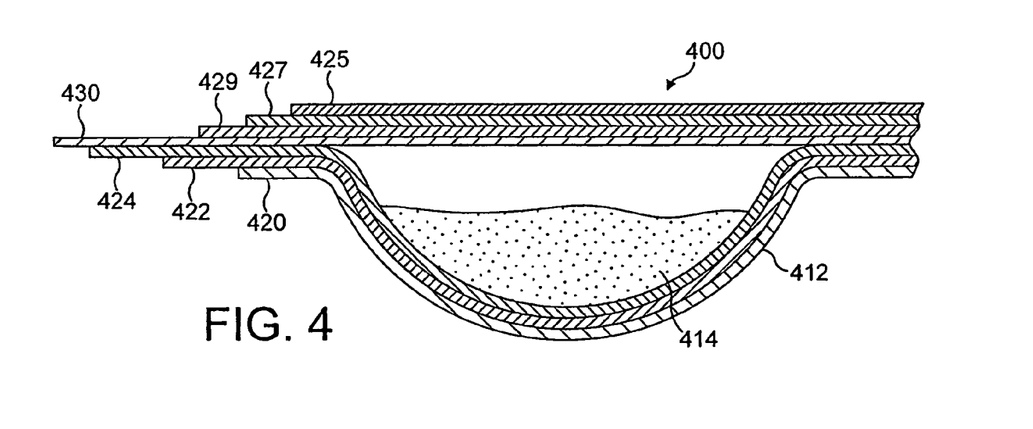
FIG. 4 shows a cross-sectional side view of the form of a laminate form medicament carrier in accord with the present invention.

Referring now to FIG. 4, the lid of the blister pack 400 has a multi-layer structure and comprises the following successive layers: paper 425 adhesively bonded to polyester 427 adhesively bonded to aluminium foil 429 that is coated with a heat seal lacquer 430. The base also has a multi-layer structure and comprises at least the following successive layers: oriented polyamide (OPA) 420 adhesively bonded to aluminium foil 422 adhesively bonded to a third polymer layer 424. The blister pack 400 is filled with inhalable medicament 414 in dry powdered form.

It will be appreciated that in variations of the blister pack of FIG. 4 different polymers may be used for the third polymer layer of the base sheet provided that the requirement is satisfied for the polymer to have a water vapour permeability of less than 0.6 g/(100 inches$^2$) (24 hours) (mil) at 25° C. measured by ASTM E96-635 (E).

In one particular variation, the base sheet of the blister pack of FIG. 4 has the following structure: 25 micron layer thickness oriented polyamide (OPA) 420; adhesively bonded to 45 micron thickness aluminium foil 422; adhesively bonded to 30 micron thickness polyvinylidene chloride (PVDC) 424 having a water vapour permeability of less than 0.6 g/(100 inches$^2$) (24 hours) (mil) at 25° C. measured by ASTM E96-635 (E).

In another particular variation, the base sheet of the blister pack of FIG. 4 has the following structure: 25 micron-layer thickness oriented polyamide (OPA) 420; adhesively bonded to 60 micron thickness aluminium foil 422; adhesively bonded to 20 micron thickness oriented polypropylene 424 having a water vapour permeability of less than 0.6 g/(100 inches$^2$) (24 hours) (mil) at 25° C. measured by ASTM E96-635 (E).

In another particular variation, the base sheet of the blister pack of FIG. 4 has the following structure: 25 micron layer thickness oriented polyamide (OPA) 420; adhesively bonded to 60 micron thickness aluminium foil 422; adhesively bonded to 25 micron thickness cast polypropylene 424 having a water vapour permeability of less than 0.6 g/(100 inches$^2$) (24 hours) (mil) at 25° C. measured by ASTM E96-635 (E).

In another particular variation, the base sheet of the blister pack of FIG. 4 has the following structure: 25 micron layer thickness oriented polyamide (OPA) 420; adhesively bonded to 60 micron thickness aluminium foil 422; adhesively bonded to 20 micron thickness oriented polypropylene 424 having a water vapour permeability of less than 0.6 g/(100 inches$^2$) (24 hours) (mil) at 25° C. measured by ASTM E96-635 (E).

In another particular variation, the base sheet of the blister pack of FIG. 4 has the following structure: 25 micron layer thickness oriented polyamide (OPA) 420; adhesively bonded to 60 micron thickness aluminium foil 422; adhesively bonded to 25 micron thickness cast polypropylene 424 having a water vapour permeability of less than 0.6 g/(100 inches$^2$) (24 hours) (mil) at 25° C. measured by ASTM E96-635 (E).

In another particular variation, the base sheet of the blister pack of FIG. 4 has the following structure: 25 micron layer thickness oriented polyamide (OPA) 420; adhesively bonded to 60 micron thickness aluminium foil 422; adhesively bonded to 25 micron thickness polypropylene 424, wherein the polypropylene is manufactured by a process in which one or more metallocene compounds are employed to control side-chain characteristics thereof, having a water vapour permeability of less than 0.6 g/(100 inches$^2$) (24 hours) (mil) at 25° C. measured by ASTM E96-635 (E).

In another particular variation, the base sheet of the blister pack of FIG. 4 has the following structure: 25 micron layer thickness oriented polyamide (OPA) 420; adhesively bonded to 60 micron thickness aluminium foil 422; adhesively bonded to 40 micron thickness low density polyethylene (LDPE) 424 having a water vapour permeability of less than 0.6 g/(100 inches$^2$) (24 hours) (mil) at 25° C. measured by ASTM E96-635 (E).

In another particular variation, the base sheet of the blister pack of FIG. 4 has the following structure: 25 micron layer thickness oriented polyamide (OPA) 420; adhesively bonded to 60 micron thickness aluminium foil 422; adhesively bonded to 40 micron thickness high density polyethylene (HDPE) 424 having a water vapour permeability of less than 0.6 g/(100 inches$^2$) (24 hours) (mil) at 25° C. measured by ASTM E96-635 (E).

In another particular variation, the base sheet of the blister pack of FIG. 4 has the following structure: 25 micron layer thickness oriented polyamide (OPA) 420; adhesively bonded to 60 micron thickness aluminium foil 422; adhesively bonded to 20 micron thickness polychlorotrifluoroethylene (PCTFE) 424 having a water vapour permeability of less than 0.6 g/(100 inches$^2$) (24 hours) (mil) at 25° C. measured by ASTM E96-635 (E). In a particular embodiment, the PCTFE is polymeric material sold under the trade name Aclar by Honeywell Inc, a United States corporation.

In another particular variation, the base sheet of the blister pack of FIG. 4 has the following structure: 25 micron layer thickness oriented polyamide (OPA) 420; adhesively bonded to 60 micron thickness aluminium foil 422; adhesively bonded to 25 micron thickness cyclic olefin copolymer (COC) 424 having a water vapour permeability of less than 0.6 g/(100 inches$^2$) (24 hours) (mil) at 25° C. measured by ASTM E96-635 (E). In a particular embodiment, the cyclic olefin copolymer (COC) is a material sold by Hoechst AG of Germany, under the trade name Topaz.

In another particular variation, the base sheet of the blister pack of FIG. 4 has the following structure: 25 micron layer thickness oriented polyamide (OPA) 420; adhesively bonded to 60 micron thickness aluminium foil 422; adhesively bonded to 25 micron thickness cyclic olefin polymer (COP) 424 having a water vapour permeability of less than 0.6 g/(100 inches$^2$) (24 hours) (mil) at 25° C. measured by ASTM E96-635 (E).

As will be appreciated by one having ordinary skill in the art, various conventional adhesives can be employed to bond the laminate layers within the scope of the invention. Such adhesives include, but are not limited to, cyanoacrylates, acrylics and polyurethanes.

During a typical blister strip manufacturing process, each blister 412 is filled with a pharmaceutical composition 414 and subsequently sealed. The sealing temperature and other parameters of the sealing method may be varied including tooling, dwell time, sealing pressure and speed of sealing. The heat-sealing step bonds the mating layers (e.g., PVC 424 and heat seal lacquer 430) of the base and lid to seal each blister 412 and, hence forms a secure container for the pharmaceutical composition 414 contained therein. Ideally, the bonding creates a hermetic seal that is formed. As will be appreciated, hermetically sealing each blister 412 to eliminate the possibility of contamination from the external environment can be an important aspect of the manufacturing process.

Various bonding schemes and patterns have been employed to bond and seal blister strips. Illustrative are the bonding schemes and patterns shown in FIGS. 2 and 3.

Referring now to FIG. 2, there is shown a bonding scheme that employs substantially uniformly distributed heat across at least one surface of the blister strip 200 to create discrete bond areas of the mating base 209 and lid surfaces. Although various bond patterns can be formed by this bonding scheme (e.g., zig-zag, dot, checkered, etc.), a checkered grid 216 pattern is employed in this example.

As illustrated in FIG. 2, the grid 216 provides a restricted, tortuous path (designated generally by Arrow M) for the ingress of contaminants and/or moisture into the blisters 203, 205, 207.

Figure 3:
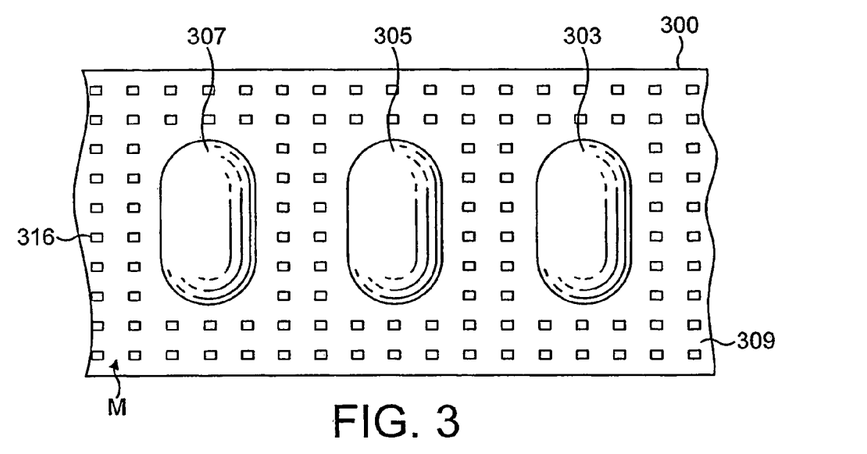
FIG. 3 shows a top view of the form of another medicament carrier of a form suitable for use in accord with the present invention.

Referring now to FIG. 3, there is shown a further bonding scheme that employs substantially uniformly distributed heat across at least one surface of the blister strip 300 to create discrete bond areas of the mating base 309 and lid surfaces. A knurled form bond pattern 316 is employed in this example. The knurling 316 provides a restricted, tortuous path (designated generally by Arrow M) for the ingress of contaminants and/or moisture into the blisters 303, 305, 307.

The medicament pack and related medicament dispenser device of the invention is suitable for dispensing medicament products particularly for the treatment of respiratory disorders such as asthma and chronic obstructive pulmonary disease (COPD), bronchitis and chest infections.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)purin-9-yl]-5-(2-ethyl-2H-tetrazol-5-yl)-tetrahydro-furan-3,4-diol (e.g. as maleate); α$_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

The medicament product may in aspects, be a monotherapy (i.e. single active medicament containing) product or it may be a combination therapy (i.e. plural active medicaments containing) product.

Suitable medicaments or medicament components of a combination therapy product are typically selected from the group consisting of anti-inflammatory agents (for example a corticosteroid or an NSAID), anticholinergic agents (for example, an $M_1$, $M_2$, $M_1/M_2$ or $M_3$ receptor antagonist), other β$_2$-adrenoreceptor agonists, antiinfective agents (e.g. an antibiotic or an antiviral), and antihistamines. All suitable combinations are envisaged.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other β$_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Suitable phosphodiesterase 4 (PDE4) inhibitors include compounds that are known to inhibit the PDE4 enzyme or which are discovered to act as a PDE4 inhibitor, and which are only PDE4 inhibitors, not compounds which inhibit other members of the PDE family as well as PDE4. Generally it is preferred to use a PDE4 inhibitor which has an IC$_{50}$ ratio of about 0.1 or greater as regards the IC$_{50}$ for the PDE4 catalytic form which binds rolipram with a high affinity divided by the IC$_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4).

This term "HPDE4" should not be confused with the term "hPDE4" which is used to denote human PDE4.

A method for determining IC$_{50}$s ratios is set out in U.S. Pat. No. 5,998,428 which is incorporated herein in full by reference as though set out herein. See also PCT application WO 00/51599 for an another description of said assay.

Suitable PDE4 inhibitors include those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an IC$_{50}$ ratio of about 0.1 or greater as regards the IC$_{50}$ for the PDE4 catalytic form which binds rolipram with a high affinity divided by the IC$_{50}$ for the form which binds rolipram with a low affinity.

A further refinement of this standard is that of one wherein the PDE4 inhibitor has an IC$_{50}$ ratio of about 0.1 or greater; said ratio is the ratio of the IC$_{50}$ value for competing with the binding of 1 nM of [$^3$H]R-rolipram to a form of PDE4 which binds rolipram with a high affinity over the IC$_{50}$ value for inhibiting the PDE4 catalytic activity of a form which binds rolipram with a low affinity using 1 μM[$^3$H]-cAMP as the substrate.

Most suitable are those PDE4 inhibitors which have an IC$_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an IC$_{50}$ ratio of 0.1 or greater.

Other suitable medicament compounds include: cis-4-cyano-4-[3-(cyclopentyloxy)-4-methoxyphenyl]cyclohexane-1-carboxylic acid (also known as cilomalast) disclosed in U.S. Pat. No. 5,552,438 and its salts, esters, pro-drugs or physical forms; AWD-12-281 from elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D4418 from Chiroscience and Schering Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Suitable anticholinergic agents are those compounds that act as antagonists at the muscarinic receptor, in particular those compounds, which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines.

Particularly suitable anticholinergics include ipratropium (e.g. as the bromide), sold under the name Atrovent, oxitropium (e.g. as the bromide) and totropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chiropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Particularly suitable anti-histamines include methapyrilene and loratadine.

In respect of combination products, co-formulation compatibility is generally determined on an experimental basis by known methods and may depend on chosen type of medicament dispenser action.

The medicament components of a combination product are suitably selected from the group consisting of anti-inflammatory agents (for example a corticosteroid or an NSAID), anti-cholinergic agents (for example, an $M_1$, $M_2$, $M_1/M_2$ or $M_3$ receptor antagonist), other $\beta_2$-adrenoreceptor agonists, anti-infective agents (e.g. an antibiotic or an antiviral), and anti-histamines. All suitable combinations are envisaged.

Suitably, the co-formulation compatible components comprise a $\beta_2$-adrenoreceptor agonist and a corticosteroid; and the co-formulation incompatible component comprises a PDE-4 inhibitor, an anti-cholinergic or a mixture thereof. The $\beta_2$-adrenoreceptor agonists may for example be salbutamol (e.g., as the free base or the sulphate salt) or salmeterol (e.g., as the xinafoate salt) or formoterol (eg as the fumarate salt). The corticosteroid may for example, be a beclomethasone ester (e.g., the dipropionate) or a fluticasone ester (e.g., the propionate) or budesonide.

In one example, the co-formulation compatible components comprise fluticasone propionate and salmeterol, or a salt thereof (particularly the xinafoate salt) and the co-formulation incompatible component comprises a PDE-4 inhibitor, an anti-cholinergic (e.g. ipratropium bromide or tiotropium bromide) or a mixture thereof.

In another example, the co-formulation compatible components comprise budesonide and formoterol (e.g. as the fumarate salt) and the co-formulation incompatible component comprises a PDE-4 inhibitor, an anti-cholinergic (e.g. ipratropium bromide or tiotropium bromide) or a mixture thereof.

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

The medicament pack and dispenser device of the invention is in one aspect suitable for dispensing medicament for the treatment of respiratory disorders such as disorders of the lungs and bronchial tracts including asthma and chronic obstructive pulmonary disorder (COPD). In another aspect, the invention is suitable for dispensing medicament for the treatment of a condition requiring treatment by the systemic circulation of medicament, for example migraine, diabetes, pain relief e.g. inhaled morphine.

Accordingly, there is provided the use of a medicament pack and dispenser device according to the invention for the treatment of a respiratory disorder, such as asthma and COPD. Alternatively, the present invention provides a method of treating a respiratory disorder such as, for example, asthma and COPD, which comprises administration by inhalation of an effective amount of medicament product as herein described from a medicament pack or dispenser device of the present invention.

The amount of any particular medicament compound or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The medicaments for treatment of respiratory disorders herein may for example, be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1 mg per day.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims.

The invention claimed is:

1. A blister form medicament pack adapted for use in an inhalation device comprising
(a) a base sheet in which blisters are formed to define pockets therein, the pockets containing inhalable medicament in dry powder form;
(b) a lid sheet which is sealed to the base sheet except in the region of the blisters and mechanically peelable from the base sheet to enable release of said inhalable medicament,
wherein said base sheet has a laminate structure comprising (a) a first layer of aluminium foil; and (b) a second layer of polymeric material of thickness from 10 to 60 micron, said polymeric material having a water vapour permeability of less than 0.6 g /(100 inches$^2$) (24 hours) (mil) at 25° C.

2. A blister form medicament pack according to claim 1, wherein the polymeric material is selected from the group consisting of: polypropylene; polyethylene; polyvinylidene chloride (PVDC); polychlorotrifluoroethylene (PCTFE); cyclic olefin copolymer (COC); and cyclic olefin polymer (COP).

3. A blister form medicament pack according to claim 2, wherein the polymeric material is polypropylene having a form selected from the group consisting of oriented or cast form.

4. A blister form medicament pack according to claim 2, wherein the polymeric material is polyethylene having a form selected from the group consisting of high, low or intermediate density form.

5. A blister form medicament pack according to claim 1, in the form of an elongate peelable blister strip having multiple distinct blister portions provided along its length.

6. A blister form medicament pack according to claim 1, wherein the polymeric material of the second layer has a water vapour permeability of less than 0.3 g/(100 inches$^2$) (24 hours) (mil) at 25° C.

7. A blister form medicament pack according to claim 1, wherein the thickness of the second layer is from 20 to 30 micron.

8. A blister form medicament pack according to claim 1, wherein the second layer is an inner layer of the pack.

9. A blister form medicament pack according to any of claims 1 to 8, wherein the lid sheet comprises at least the following successive layers: (a) paper; bonded to (b) plastic film; bonded to (c) aluminium foil.

10. A blister form medicament pack according to claim 9, wherein the aluminium foil is further provided with a layer of heat seal lacquer.

11. A blister form medicament pack according to claim 9, wherein said plastic film layer comprises a material selected from the group consisting of polyester, polyamide, polypropylene and PVC.

12. A blister form medicament pack according to claim 11, wherein the plastic film is an oriented plastic film comprising a material selected from the group consisting of oriented polyamide (OPA), oriented polyester (OPET), and oriented polypropylene (OPP).

13. A blister form medicament pack according to claim 11, wherein the plastic layer has a thickness of from 5 to 40 μm.

14. A blister form medicament pack according to claim 9, wherein the aluminium layer has a thickness of from 15 to 60 μm.

15. A blister form medicament pack according to claim 1, wherein the base sheet comprises at least the following successive layers: (a) oriented polyamide (OPA); adhesively bonded to (b) aluminium foil; adhesively bonded to (c) a layer of thickness from 10 to 60 micron comprising the polymeric material having a water vapour permeability of less than 0.6 g/(100 inches$^2$) (24 hours) (mil) at 25° C.

16. A blister form medicament pack according to claim 15, wherein the polymeric material comprises oriented polypropylene (OPP) and the thickness of the polymeric layer is from 20 to 30 micron.

17. A blister form medicament pack according to claim 15, wherein the polymeric material comprises cast polypropylene and the thickness of the polymeric layer is from 20 to 30 micron.

18. A blister form medicament pack according to claim 15, wherein the polymeric material comprises high density polyethylene (HDPE) and the thickness of the polymeric layer is from 35 to 45 micron.

19. A blister form medicament pack according to claim 15, wherein the polymeric material comprises low density polyethylene (LDPE) and the thickness of the polymeric layer is from 20 to 30 micron.

20. A blister form medicament pack according to claim 15, wherein the polymeric material comprises polyvinylidene chloride (PVDC) and the thickness of the polymeric layer is from 20 to 30 micron.

21. A blister form medicament pack according to claim 15, wherein the polymeric material comprises polychlorotrifluoroethylene (PCTFE) and the thickness of the polymeric layer is 20 to 45 micron.

22. A blister form medicament pack according to claim 15, wherein the polymeric material comprises cyclic olefin copolymer (COC) and the thickness of the polymeric layer is from 20 to 30 micron.

23. A blister form medicament pack according to claim 1, wherein said inhalable medicament comprises one or more medicament actives selected from the group consisting of anti-inflammatory agents, anticholinergic agents, other $\beta_2$-adrenoreceptor agonists, antiinfective agents, antihistamines and any mixtures thereof.

24. A blister form medicament pack according to claim 23, wherein said anti-inflammatory agents are selected from the group consisting of corticosteroids, NSAIDs and any mixtures thereof.

25. A blister form medicament pack according to claim 24, wherein said corticosteroids are selected from the group consisting of methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy- androsta-1,4-diene-17β-carbothioic acid S-(2-oxo-tetrahydro-furan-3S-yl) ester, beclomethasone esters, flunisolide, mometasone esters, triamcinolone acetonide, rofleponide, ciclesonide, butixocort propionate, RPR-106541, and ST-126 and any mixtures thereof.

26. A blister form medicament pack according to claim 24, wherein said NSAIDs are selected from the group consisting of sodium cromoglycate, nedocromil sodium, phosphodiesterase (PDE) inhibitors, leukotriene antagonists, inhibitors of leukotriene synthesis, iNOS inhibitors, tryptase and elastase inhibitors, beta-2 integrin antagonists, adenosine receptor agonists or antagonists, cytokine antagonists, inhibitors of cytokine synthesis and any mixtures thereof.

27. A blister form medicament pack adapted for use in an inhalation device comprising:
  (a) a base sheet in which blisters are formed to define pockets therein for the containment of inhalable medicament;
  (b) a lid sheet which is sealed to the base sheet except in the region of the blisters and mechanically peelable from the base sheet to enable release of said inhalable medicament,
  wherein one or more of the blisters contain inhalable medicament in dry powder form, and said base sheet has a laminate structure comprising at least the following successive layers: (a) oriented polyamide (OPA); adhesively bonded to (b) aluminum foil; adhesively bonded to (c) an inner layer of polymeric material of thickness from 10 to 60 micron, said polymeric material having a water vapour permeability of less than 0.6 g/(100 inches$^2$) (24 hours) (mil) at 25 C, said lid sheet has a laminate structure comprising at least the following successive layers: (a) paper; bonded to (b) plastic film; bonded to (c) aluminum foil, and said aluminum foil layer of the lid sheet has a coating layer for bonding to the base sheet, the coating layer selected from the group consisting of heat seal lacquer, film and extrusion coating.

28. A blister form medicament pack according to claim 1, wherein the second layer is disposed inwardly of the first layer with respect to the lid sheet.

29. A blister form medicament pack according to claim 28, wherein the lid sheet and the base sheet are sealed together through a bonding material which bonds an inner face of the lid sheet to an inner face of the base sheet which is presented by the second layer.

30. A blister form medicament pack according to claim 29, wherein the first and second layers of the base sheet are successive layers of the base sheet which are bonded together.

31. A blister form medicament pack according to claim 30, wherein the polymeric material of the second layer is selected from the group consisting of a polypropylene and a polyethylene.

32. A blister form medicament pack according to claim 31, wherein the base sheet consists essentially of the first layer, the second layer and an outer layer of a polymeric material which is bonded to the first layer.

33. A blister form medicament pack according to claim 32, wherein the outer layer is of an oriented polyimide.

* * * * *